(12) United States Patent
Utsugi et al.

(10) Patent No.: US 8,545,757 B2
(45) Date of Patent: Oct. 1, 2013

(54) AUTOMATIC ANALYZER AND SAMPLE TREATMENT APPARATUS

(75) Inventors: Yasushi Utsugi, Hitachinaka (JP); Kuniaki Onizawa, Hitachinaka (JP); Ken Takakura, Tokai (JP); Yoshio Kiyonari, Hitachinaka (JP); Isao Yamazaki, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 89 days.

(21) Appl. No.: 13/146,582

(22) PCT Filed: Jan. 18, 2010

(86) PCT No.: PCT/JP2010/000213
§ 371 (c)(1),
(2), (4) Date: Sep. 9, 2011

(87) PCT Pub. No.: WO2010/087120
PCT Pub. Date: Aug. 5, 2010

(65) Prior Publication Data
US 2012/0039771 A1    Feb. 16, 2012

(30) Foreign Application Priority Data
Jan. 30, 2009  (JP) ................. 2009-018941

(51) Int. Cl.
*B01L 3/02*    (2006.01)
(52) U.S. Cl.
USPC ............. 422/67; 422/63; 422/68.1; 422/501; 422/509; 422/516; 422/517; 422/518; 73/864.02

(58) Field of Classification Search
USPC ......... 422/501, 504–505, 508–509, 516–518, 422/521–522, 107, 112, 63–68.1; 73/864.02
See application file for complete search history.

(56) References Cited

U.S. PATENT DOCUMENTS

| | | | | |
|---|---|---|---|---|
| 5,013,529 A | * | 5/1991 | Itoh ................................ | 422/511 |
| 5,158,748 A | * | 10/1992 | Obi et al. ...................... | 422/511 |
| 5,380,486 A | * | 1/1995 | Anami ........................... | 422/63 |
| 5,665,601 A | * | 9/1997 | Kilmer .......................... | 436/54 |
| 5,935,859 A | * | 8/1999 | Elliott et al. ................... | 506/33 |
| 6,100,094 A | * | 8/2000 | Tajima .......................... | 436/54 |
| 6,121,049 A | * | 9/2000 | Dorenkott et al. ............. | 436/50 |
| 6,521,187 B1 | * | 2/2003 | Papen .......................... | 422/504 |
| 6,592,825 B2 | * | 7/2003 | Pelc et al. ..................... | 422/521 |

(Continued)

FOREIGN PATENT DOCUMENTS

| | | |
|---|---|---|
| JP | 6-174731 A | 6/1994 |
| JP | 2005-207898 A | 8/2005 |
| JP | 2005-265689 A | 9/2005 |
| JP | 2007-316011 A | 12/2007 |

*Primary Examiner* — Brian R Gordon
(74) *Attorney, Agent, or Firm* — Mattingly & Malur, PC

(57) ABSTRACT

A sample treatment apparatus is designed to directly monitor a pressure signal from a pressure sensor to examine pressure fluctuations resulting from a sample's sway before a discharge of the sample, so that the discharge is performed after the confirmation of the absence of pressure changes. The apparatus has a detection function that allows a discharge to be started even before a pressure fluctuation vanishes completely, by allowing the operator to set a desired number of pressure monitorings, monitoring time, or pressure amplitude. The detection function also allows an alarm to be raised when a pressure fluctuation has not fallen within a given range. The sample treatment apparatus therefore allows discharge of more accurate amounts of samples.

8 Claims, 8 Drawing Sheets

(56) References Cited

U.S. PATENT DOCUMENTS

| | | | |
|---|---|---|---|
| 6,937,955 B2 * | 8/2005 | Barnes | 702/94 |
| 7,314,598 B2 * | 1/2008 | Nishino | 422/501 |
| 7,396,512 B2 * | 7/2008 | DiTrolio et al. | 422/522 |
| 7,470,547 B2 * | 12/2008 | Tisone et al. | 436/180 |
| 7,581,660 B2 * | 9/2009 | Nay et al. | 222/61 |
| 7,846,384 B2 * | 12/2010 | Watson et al. | 422/63 |
| 7,964,160 B2 * | 6/2011 | Zuppiger et al. | 422/500 |
| 7,976,794 B2 * | 7/2011 | Trump | 422/501 |
| 8,075,840 B2 * | 12/2011 | Shimane et al. | 422/63 |
| 8,088,343 B2 * | 1/2012 | Kakizaki | 422/546 |
| 8,128,891 B2 * | 3/2012 | Takahashi | 422/500 |
| 8,221,702 B2 * | 7/2012 | Shimoda et al. | 422/527 |
| 8,257,664 B2 * | 9/2012 | Ogusu | 422/501 |
| 8,287,806 B2 * | 10/2012 | Bjornson et al. | 422/63 |
| 8,354,078 B2 * | 1/2013 | Shohmi et al. | 422/509 |
| 8,357,544 B2 * | 1/2013 | Ingenhoven et al. | 436/180 |
| 2001/0016177 A1 * | 8/2001 | Pelc et al. | 422/100 |
| 2003/0203494 A1 * | 10/2003 | Hyde et al. | 436/49 |
| 2004/0101440 A1 * | 5/2004 | Ishizawa et al. | 422/64 |
| 2005/0095723 A1 * | 5/2005 | DiTrolio et al. | 436/180 |
| 2005/0194394 A1 * | 9/2005 | Ueda et al. | 221/4 |
| 2006/0133965 A1 * | 6/2006 | Tajima et al. | 422/100 |
| 2009/0056477 A1 * | 3/2009 | Nishimura et al. | 73/864.11 |
| 2009/0060785 A1 * | 3/2009 | Shimane et al. | 422/67 |
| 2012/0114526 A1 * | 5/2012 | Watanabe et al. | 422/63 |

* cited by examiner

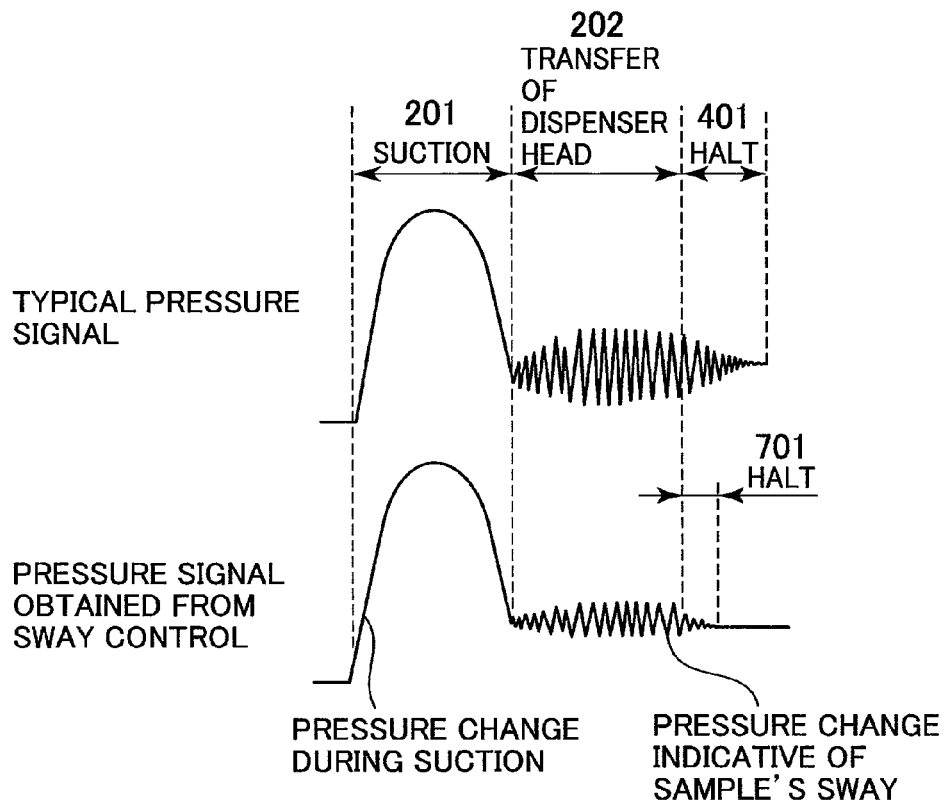
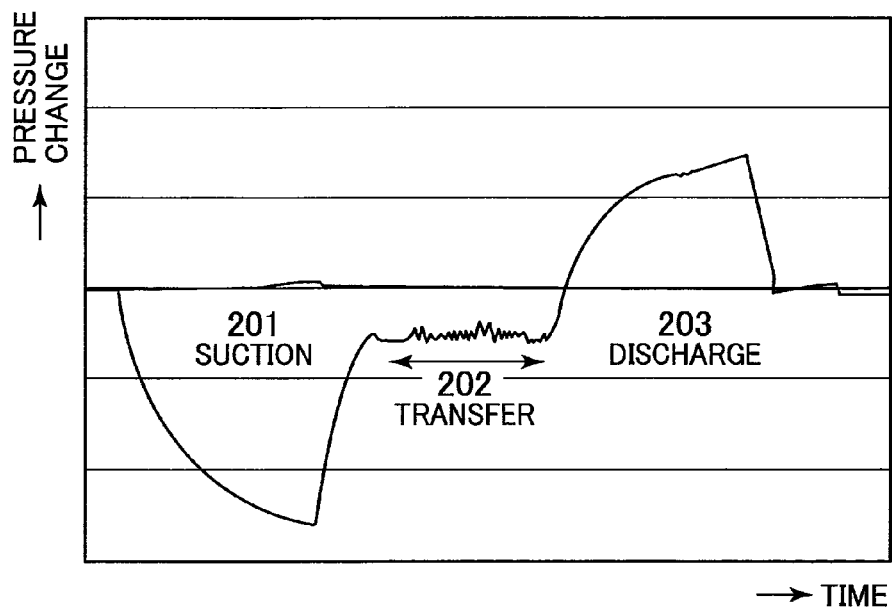

AUTOMATIC ANALYZER AND SAMPLE TREATMENT APPARATUS

TECHNICAL FIELD

The present invention relates to automatic analyzers that qualitatively and quantitatively analyze biological samples such as blood serum and urine and to sample treatment (pretreatment) apparatuses that perform centrifugal separation or other pretreatments on samples so that an automatic analyzer can analyze the samples. The invention relates particularly to an automatic analyzer and a sample treatment apparatus each with a dispensing mechanism for dispensing a given amount of a sample.

BACKGROUND ART

An automatic analyzer and a sample treatment apparatus are commonly provided with a sample dispensing mechanism, which is used to transfer a sample contained in a vessel to a different vessel for the purposes of analysis and pretreatment. Such a sample dispensing mechanism is required to dispense the desired amount of a sample accurately and at high speed. Also, due to a growing demand in recent years to reduce costs associated with clinical inspection, the amount of a reagent used per analysis now needs to be reduced. Because a reduced reagent amount inevitably leads to a decrease in the amount of a sample used per analysis, dispensing mechanisms are now required to accurately dispense even single-digit microliter volumes of samples.

Various inventions have been disclosed that allow small-quantity dispensing. For example, exploiting the knowledge that the sway of a sample inside a nozzle affects dispensing accuracy, (Patent Document 1) discloses a technique in which a discharge operation is performed after the sample' sway inside the nozzle has subsided.
Prior Art Literature
Patent Document
Patent Document 1: JP-2007-316011-A

SUMMARY OF THE INVENTION

Problem to be Solved by the Invention

The technique of Patent Document 1 is designed to set an amount of time in advance during which the sample' sway will subside and perform a discharge operation after the dispenser nozzle has been halted for that amount of time. However, the time required for such sample sway to subside may vary depending on the sample dispensing amount or on the viscosity or other physical properties of samples. Accordingly, the dispenser nozzle needs to be halted for a long time if stable dispensing is to be ensured for any sample. Thus, the above technique may result in reduced analysis capabilities.

Therefore, an object of the present invention is to provide an automatic analyzer and a sample treatment apparatus each with a dispensing mechanism which allows accurate small-quantity dispensing.

Means for Solving the Problem

The sample treatment apparatus of the invention is designed to directly monitor a pressure signal from a pressure sensor to examine pressure fluctuations resulting from a sample's sway before a discharge of the sample, so that the discharge is performed after the confirmation of the absence of pressure changes. The apparatus has a detection function that allows a discharge to be started even before a pressure fluctuation vanishes completely, by allowing the operator to set a desired number of pressure monitorings, monitoring time, or pressure amplitude. The detection function also allows an alarm to be raised when a pressure fluctuation has not fallen within a given range.

Effect of the Invention

As stated above, the detection function allows the status of a sample (suctioned, discharged, or swaying) to be examined directly from a pressure sensor signal. This in turn allows discharge of the sample after the pressure fluctuation resulting from the sample's sway due to a transfer of the dispenser head has fallen within a given range, thereby ensuring a highly accurate sample discharge. Moreover, adding a control mechanism for suppressing the sway of a sample's surface makes it possible to shorten the halt time required to suppress the pressure fluctuation resulting from the sway to within a given range.

BRIEF DESCRIPTION OF THE DRAWINGS

FIG. 3 is a flowchart of operations according to an embodiment which are performed for pressure signal fluctuations resulting from a sample's sway inside a nozzle tip and the like;

FIG. 5 is a flowchart of conditional operations according to an embodiment which are performed for pressure signal fluctuations resulting from a sample's sway inside a nozzle tip and the like;

FIG. 7 shows the effect obtained from suppressing the sway of a sample's surface;

FIG. 8 illustrates an output signal from the pressure sensor 7 during sample suction/discharge;

MODE FOR CARRYING OUT THE INVENTION

Figure 1:
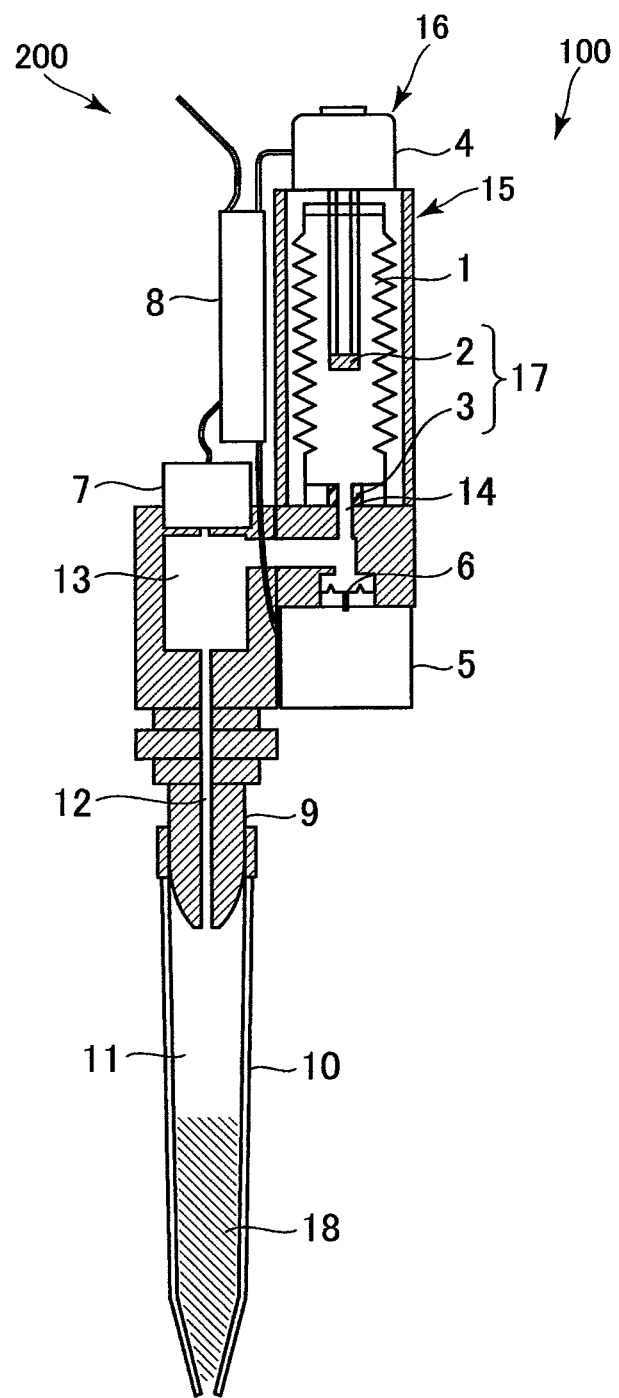
FIG. 1 illustrates the structure of a dispenser head of a sample treatment apparatus according to an embodiment.
Figure 2:
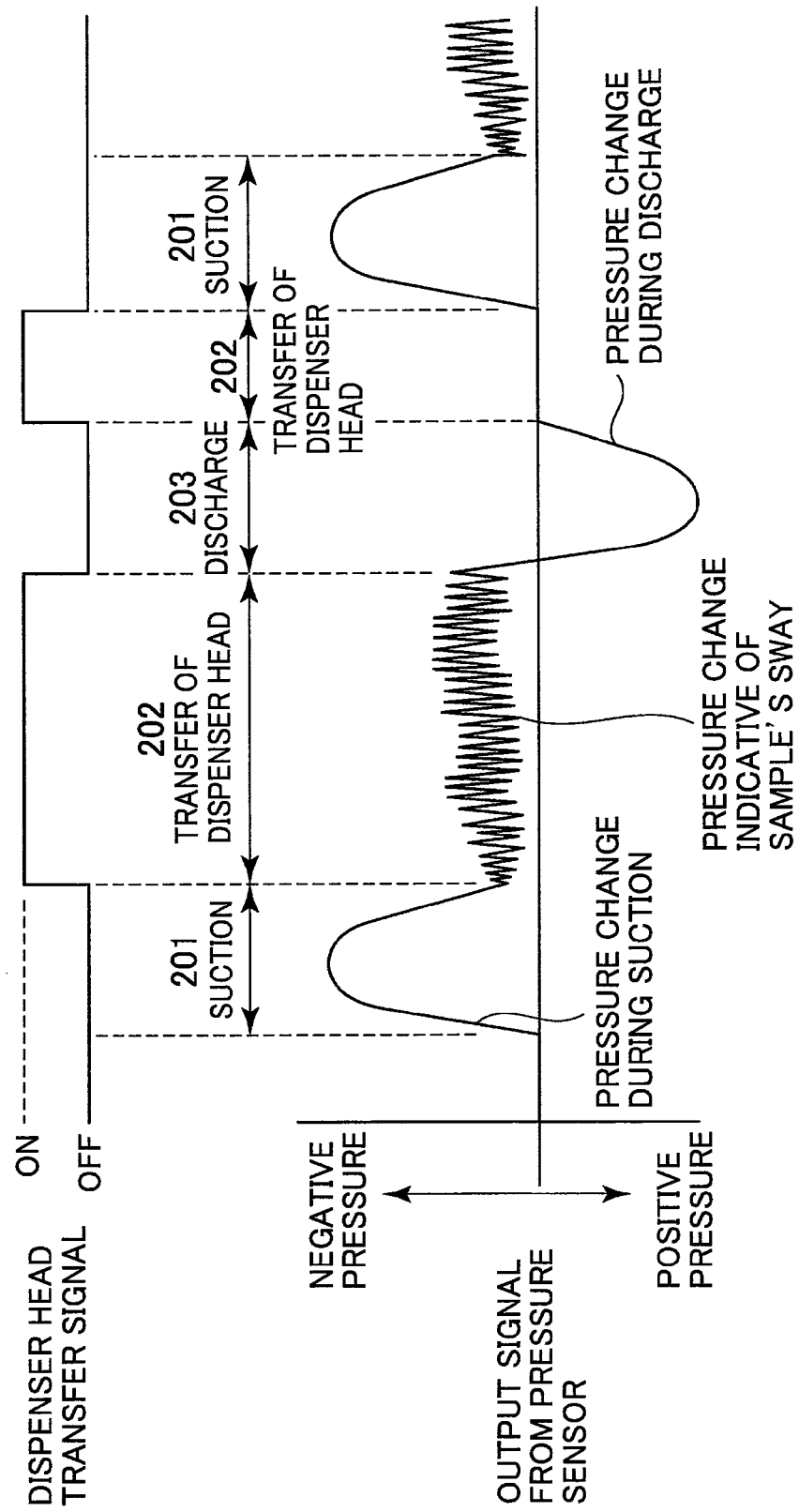
FIG. 2 shows the relationship, according to the invention, between an output signal from a pressure sensor 7 and a transfer of a dispenser head during sample suction/discharge.

The detection functions of a sample treatment apparatus according to embodiments of the invention will now be described with reference to FIGS. 1 through 7. The sample treatment apparatus includes a sample dispensing mechanism and is used for systems at hospital laboratories or inspection centers which are designed to perform blood pretreatments before blood analysis, such as automatic centrifugal treatment, removal of caps from blood tubes, and dividing serum into small quantities. FIG. 1 illustrates the structure of the dispenser head 200 of the sample treatment apparatus according to an embodiment. The dispenser head 200 of FIG. 1 includes the following main components: a nozzle base 9 attached to a casing 15; a nozzle tip 10 attached to the nozzle base 9; a bellows mechanism 100 for suctioning/discharging a sample; a pressure sensor 7 for converting into electric signals pressure changes resulting from sample suction/discharge (i.e., changes in the inner pressure of a cavity 13, described later, of the casing 15); a diaphragm 6 which act as a vibrator for vibrating the air inside cavity 13 during liquid surface detection; a solenoid 5 for driving the diaphragm 6; and a signal processor circuit 8 for sending/receiving electric signals to/from the pressure sensor 7, a motor 4, and the solenoid 5.

Inside the casing 15 are an inner space for housing a bellows 1 and a cavity 12 as well as the above-mentioned cavity 13, both of which act as air passageways communicating with the inner space of the bellows 1 through an air vent 14. The cavities 12 and 13 are also open to the outside through the nozzle base 9 and the nozzle tip 10. When the nozzle tip 10 is inserted into a sample 18, followed by expansion of the bellows 1, the sample 18 is suctioned into the nozzle tip 10 from the lower-end hole of the nozzle tip 10. Because the dispenser head 200 then needs to be moved with the sample 18 being kept inside the nozzle tip 10, the sample 18 inside the nozzle tip 10 is caused to sway. This sway of the sample 18 is detected as a pressure signal fluctuation. The lower end of the nozzle tip 10 is then inserted into a given vessel, and contraction of the bellows 1 allows discharge of the sample 18 into that vessel. The signal processor circuit 8 is connected to an external signal processor circuit (not illustrated), and a microprocessor or the like performs signal detection, dispensing control, abnormality removal, and so forth. The use of the method disclosed in JP-2005-207898-A also allows sample surface detection.

FIG. 8 shows as an example the relationship between an output signal from the pressure sensor 7 and a transfer of the dispenser head 200 during sample suction/discharge by the sample treatment apparatus. A suction operation 201 causes a pressure change inside the dispenser head 200, which is to be detected by the pressure sensor 7. Because the suction 201 is followed by a discharge operation, the dispenser head 200 is transferred (202) to the discharge position by a mechanism, not illustrated, which moves the dispenser head 200 in X-, Y-, and Z-axes. The transfer of the dispenser head 200 causes a large pressure fluctuation, and the example of FIG. 8 shows a pressure signal obtained when a discharge operation 203 is performed before the pressure fluctuation subsides.

Figure 9:
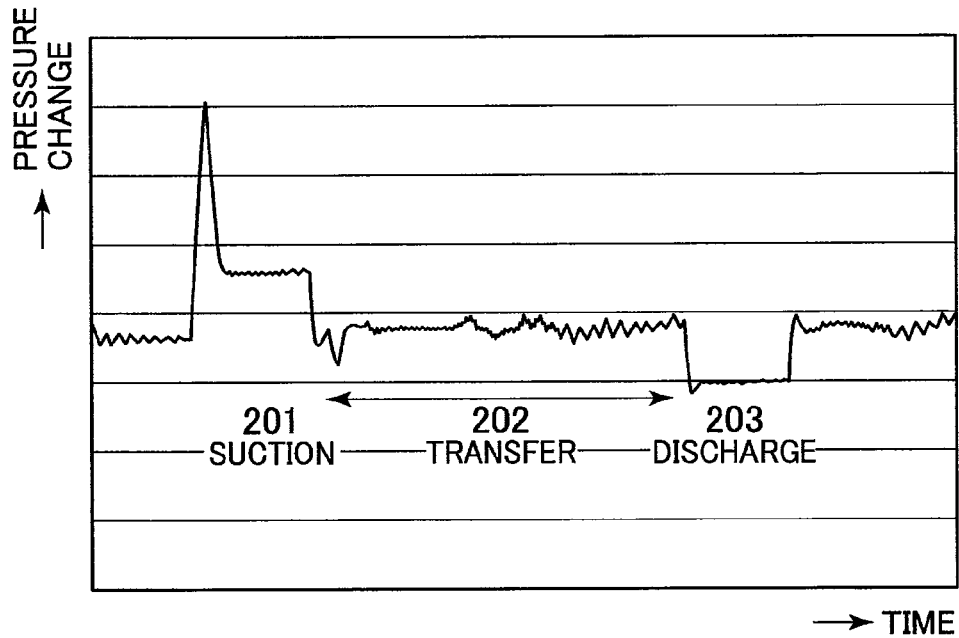
FIG. 9 illustrates an output signal from the pressure sensor 7 during sample suction/discharge.

Likewise, FIG. 9 shows as an example the relationship between an output signal from a pressure sensor and a transfer of the dispenser head during sample suction/discharge by an automatic analyzer. In the automatic analyzer as well, a suction operation 201 causes a change in the pressure detected by its pressure sensor. When the dispenser mechanism of the analyzer is then transferred (202) to the discharge position, the pressure fluctuates subtly, and in the example of FIG. 9, a discharge operation 203 is performed before the pressure fluctuation subsides. As above, if a discharge operation is performed before the pressure fluctuation resulting from a transfer of the dispenser mechanism subsides, this may affect sample dispensing amounts, especially when the amounts are required to be exact. Therefore, the present invention is designed to directly monitor changes in the pressure detected by the pressure sensor 7 of the dispenser head 200. Because a pressure change before sample discharge greatly affects the ability to achieve precise dispensing amounts, the invention is designed to monitor the pressure prior to the sample discharge and perform the discharge after confirming the absence of pressure fluctuation, thereby achieving more accurate dispensing capabilities.

Figure 3:
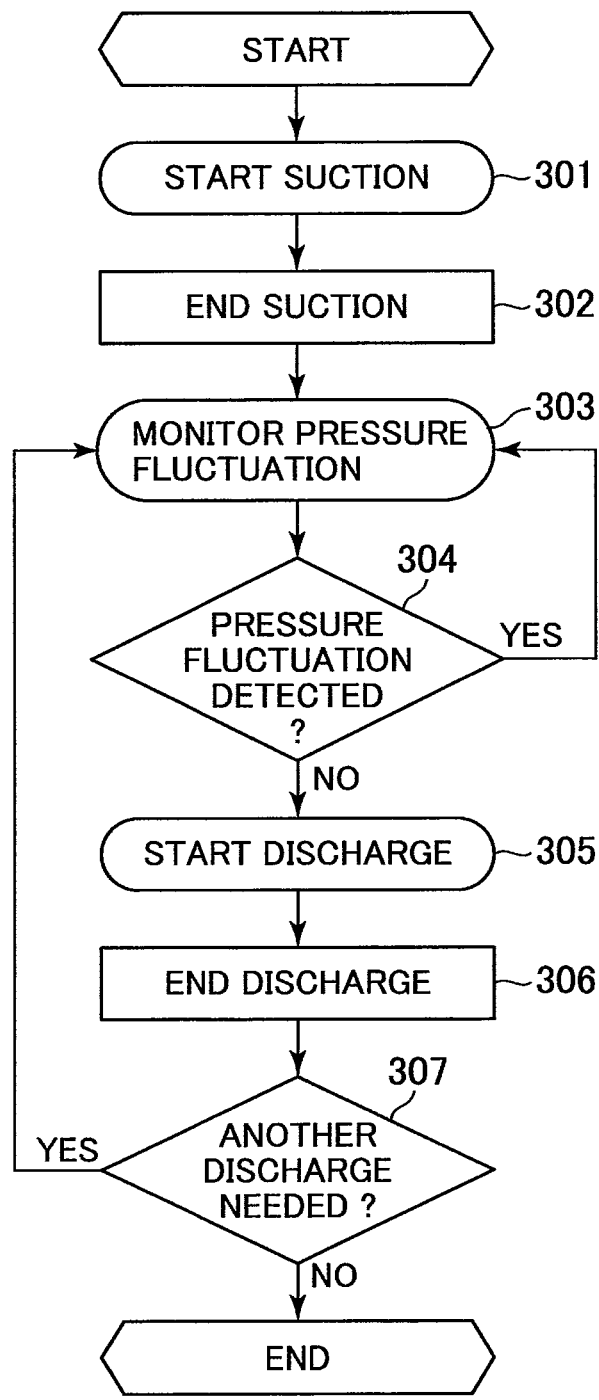

FIG. 3 is a flowchart of operations according to an embodiment which are performed for pressure signal fluctuations resulting from a sample's sway inside the nozzle tip 10 and the like. The dispenser head 200 allows direct monitoring of pressure signal fluctuations resulting from the sway of the sample 18 inside the nozzle tip 10 due to a transfer of the dispenser head 200, thereby confirming the absence of pressure signal fluctuation (the sample's sway) prior to a discharge operation. When a suction operation is started (301) to suction the sample 18 into the nozzle tip 10, the pressure signal starts to fluctuate. After the completion of the suction (302), the dispenser head 200 is transferred with a given pressure being maintained. Since the transfer of the dispenser head 200 causes the sample 18 to sway, the pressure signal from the pressure sensor 7 also fluctuates. Thus, the pressure signal is directly monitored for any sign of fluctuation (303). Detection of a pressure signal fluctuation (304) is followed by execution of a loop until the fluctuation detected from within the nozzle tip 10 vanishes. After the fluctuation is confirmed to have vanished (304), a discharge operation is started (305). When the completion of the discharge operation (306) needs to be followed by another discharge (307), the pressure signal is monitored again for fluctuation (303, 304), and the absence of fluctuation is confirmed before the subsequent discharge.

Figure 4:
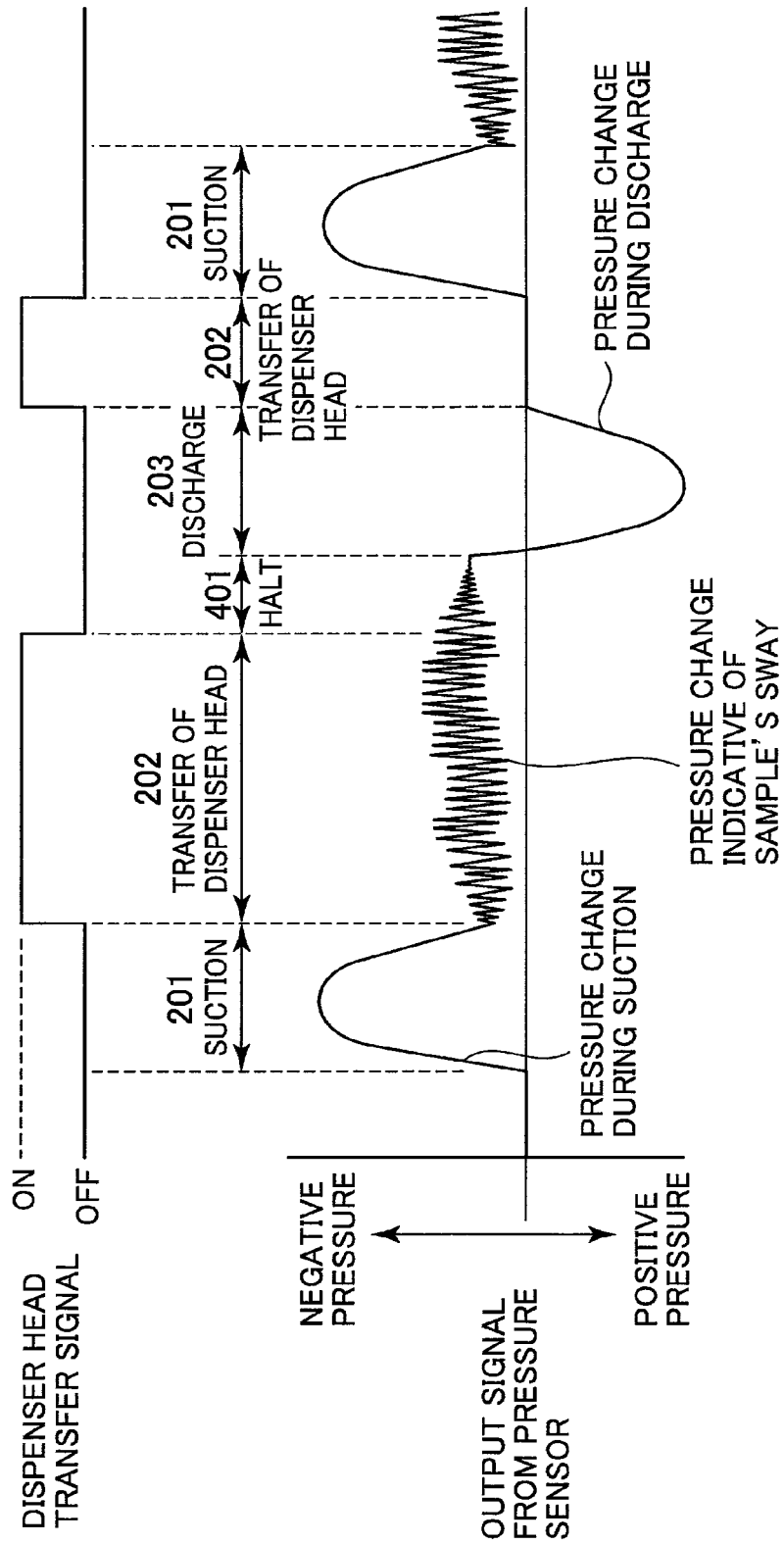
FIG. 4 shows the relationship between an output signal from a pressure sensor and a transfer of a dispenser head during sample suction/discharge when a detection function is employed.

FIG. 4 shows the relationship between an output signal from the pressure sensor 7 and a transfer of the dispenser head 200 during sample suction/discharge when a detection function is employed. The detection function allows direct monitoring of the output signal from the pressure sensor 7 between the completion of a transfer (202) of the head 200 and the start of a discharge operation (203). For the purpose of examining the presence/absence of pressure fluctuation, the dispenser head 200 is halted (401), so that the absence of pressure fluctuation is confirmed before the discharge (203). This allows an accurate amount of the sample 18 to be discharged without the sample 18 swaying inside the nozzle tip 10. In addition, even when pressure fluctuation varies depending on the suction amount, direct monitoring of the pressure fluctuation allows automatic correction of monitoring of the sample's sway.

Figure 5:
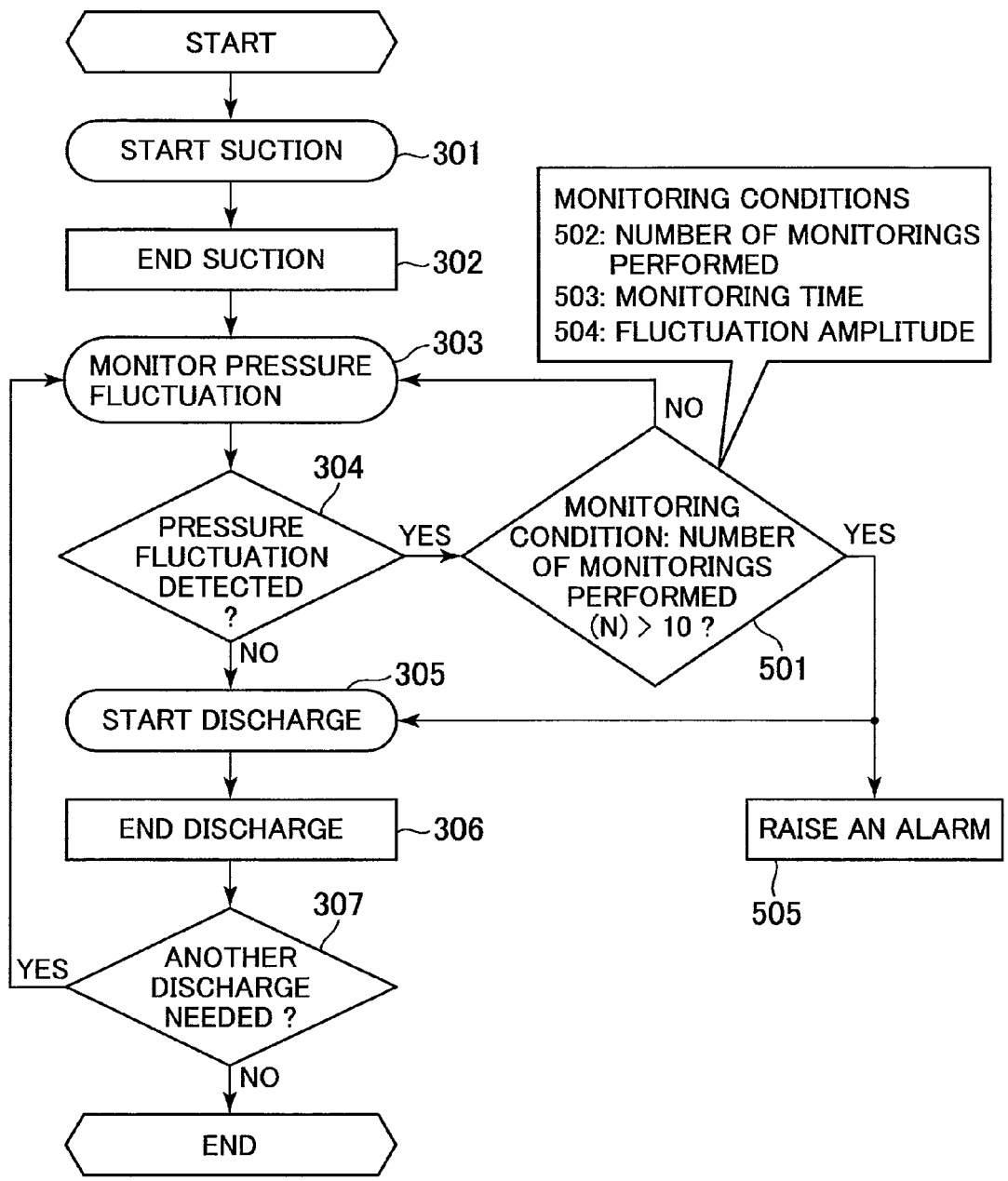

FIG. 5 is a flowchart of conditional operations according to an embodiment which are performed for pressure signal fluctuations resulting from a sample's sway inside the nozzle tip 10 and the like. The process of FIG. 3, where a discharge operation is started (305) after a pressure fluctuation detected from within the nozzle tip 10 has vanished (304), could be time-consuming. Thus, the operator is allowed to set a desired number of pressure monitorings (303) as a condition for the monitoring of pressure signal fluctuation resulting from the sway of the sample 18 inside the nozzle tip 10, so that a discharge operation can be performed when the fluctuation has vanished within the set number of monitorings. The discharge operation is performed also when the fluctuation has not vanished within the set number, but in that case, a flag is also raised to give an alarm (505). This alarm may be given to the operator as a warning message on the apparatus or its main operating unit (not illustrated). Other possible conditions (501) to be set to monitor pressure signal fluctuation include a pressure monitoring time 503, a fluctuation amplitude 504, and the like, which serve similar purposes.

Figure 6:
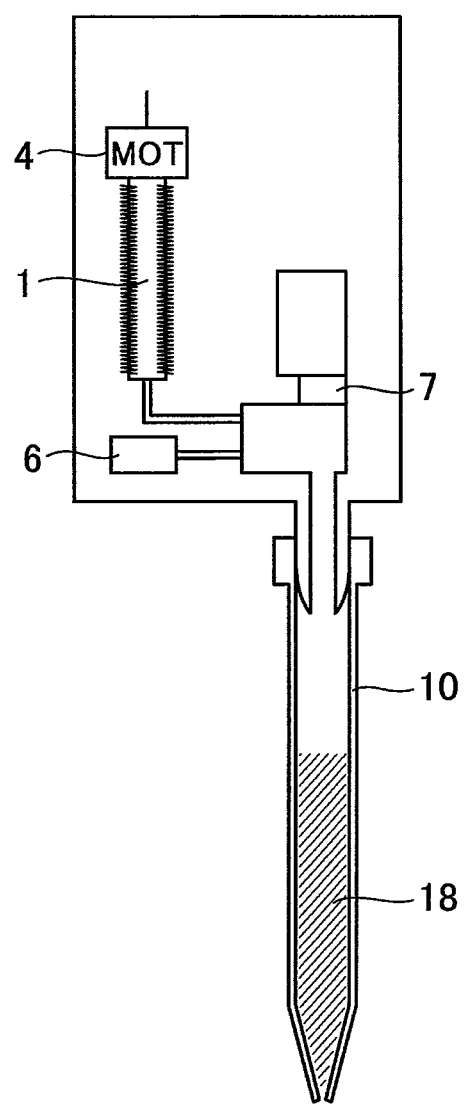
FIG. 6 illustrates the structure of a dispenser head which is designed to prevent the sway of a sample's surface.

FIG. 6 illustrates the structure of a dispenser head according to an embodiment which is designed to suppress the sway of a sample's surface, and FIG. 7 shows the effect obtained from doing so. Two methods are given below to directly monitor an output signal from the pressure sensor 7 and thereby control fluctuations in the signal (the sample's sway). One involves first directly monitoring pressure fluctuations resulting from the sway of the sample 18 inside the nozzle tip 10 and computing their cycles (i.e., frequency). The diaphragm 6 (vibrator) is then vibrated at a frequency that cancels out the computed frequency, thereby suppressing the signal fluctuations. The other method involves the use of the bellows 1. When a pressure signal obtained from within the nozzle tip 10 fluctuates from the positive side to the negative side, the motor 4 drives the bellows 1 so as to contract it, thereby applying a counter pressure. Conversely, when the pressure signal fluctuates from the negative side to the positive side, the motor 4 drives the bellows 1 so as to expand it, whereby the pressure signal fluctuation can be suppressed. The above methods allow a more accurate amount of a sample to be discharged by suppressing the sample's sway resulting from a transfer of the dispenser head (202). The methods also require, before a discharge operation, less halt time (701) to suppress the pressure fluctuation resulting from the sample's sway to within a given range.

Figure 10:
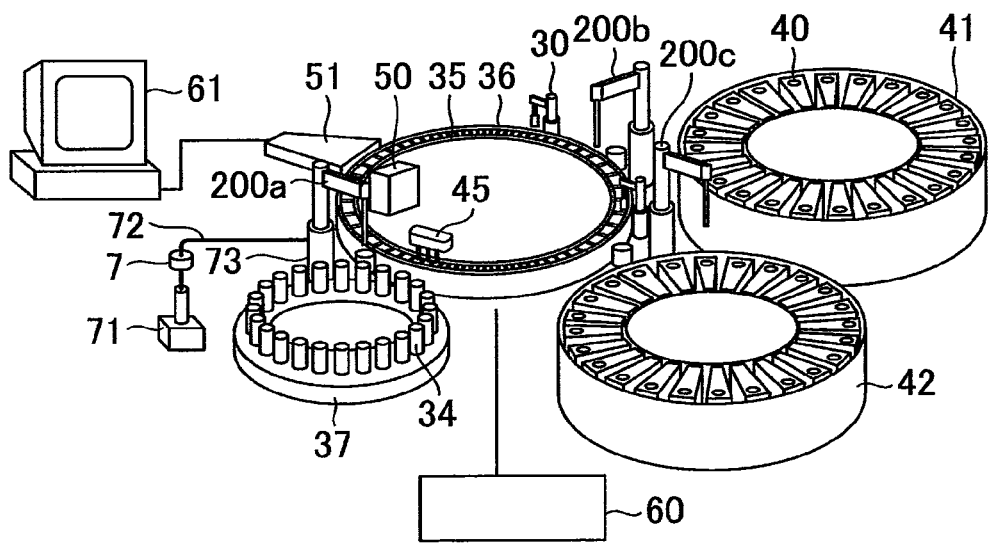
FIG. 10 illustrates the configuration of an automatic analyzer according to the invention.

FIG. 10 illustrates the configuration of an automatic analyzer to which the invention is applied.

The automatic analyzer includes the following components: a sample disk 37 for placing thereon multiple sample vessels 34 used for containing samples; first and second reagent disks 41 and 42 for placing thereon multiple reagent vessels 40 used for containing reagents; a reaction disk 36 for placing multiple reaction vessels 35 around its circumference; a sample dispenser head 200a for dispensing a sample suctioned from any of the sample vessels 34 into any of the reaction vessels 35; a first reagent dispenser head 200b for dispensing a reagent suctioned from any of the reagent vessels 40 on the first reagent disk 41 into any of the reaction vessels 35; a second reagent dispenser head 200c for dispensing a reagent suctioned from any of the reagent vessels 40 on the second reagent disk 42 into any of the reaction vessels 35; a stirrer 30 for stirring a sample-reagent mixture inside any of the reaction vessels 35; a vessel rinse mechanism 45 for rinsing the reaction vessels 35; a light source 50 installed near the outer periphery of the reaction disk 36; a spectroscopic optical system 51; a computer 61 connected to the spectroscopic optical system 51; and a controller 60 for controlling the entire operation of the analyzer and exchanging data with an external device. The sample dispenser head 200a is connected to a metering pump 71 via a tube 72. Located in the middle of the tube 72 is a pressure sensor 7. Although not illustrated, the first and second reagent dispenser heads 200b and 200c are also connected to metering pumps and pressure sensors. Further, the sample dispenser head 200a is attached to a drive mechanism 73 that can move vertically and rotate.

The following describes the operation of the automatic analyzer of this embodiment. Blood samples or other analytes are put into the sample vessels 34, and the sample vessels 34 are then placed on the sample disk 37. The type of analysis to be performed on each sample is input to the controller 60. The sample disperser head 200a suctions a sample and dispenses a given amount of the sample to some of the reaction vessels 35 on the reaction disk 36, and the reagent dispenser head 20 or 21 dispenses a given amount of a reagent from one of the reagent vessels 40 placed on the reagent disk 41 or 42 into those reaction vessels 35. The resultant sample-reagent mixtures are stirred by the stirrer 30. The reaction disk 36 rotates and stops in an alternate manner according to given cycles, and photometry is performed by detecting an output signal from the spectroscopic optical system 51 when each of the reaction vessels 35 passes the light source 50. The photometry is performed repeatedly during a reaction time of 10 minutes. Thereafter, the vessel rinse mechanism 45 empties and rinses the reaction vessels 35 that have undergone the photometry. In the meantime, the other reaction vessels 35 are also subjected to such operations as above in which different samples and reagents are used. The computer 61 calculates the concentration of the substance of interest in a sample based on the result of photometry performed during its reaction time and outputs the calculated concentration.

The following describes how to dispense a sample. The inner passageways of the metering pump 71, the tube 72, and the sample dispenser head 200a are filled with water. The controller 60 instructs the drive mechanism 73 to rotate so as to transfer the sample dispenser head 200a to a position above one of the sample vessels 34. The metering pump 71 then performs a suction operation so that the sample dispenser head 200a can suction a small amount of air into its tip. Next, the drive mechanism 73 is lowered to insert the sample dispenser head 200a into the sample inside that sample vessel 34, and this is followed by a suction operation by the metering pump 71 so that the sample dispenser head 200a can suction part of the sample. The drive mechanism 71 is then lifted, rotated, and lowered to insert the sample dispenser head 200a into one of the reaction vessels 35. During the above operations, the pressure sensor 7 measures the pressure fluctuation inside the inner passageways and transmits the pressure data to the controller 60. The controller 60 analyzes the pressure data, thereby instructing the metering pump 71 to start a discharge operation after the pressure fluctuation has been suppressed to within a given range. After the sample discharge, the drive mechanism 73 is lifted and rotated. The inner passageway and the outer structure of the sample dispenser head 200a are then rinsed by a rinse mechanism not illustrated, thereby making the dispenser head 200a ready for next sample dispensing.

Reagent dispensing is performed in the same manner as sample dispensing.

In the present embodiment, the distance between the metering pump 71 and the sample dispenser head 200a is long, and the passageway connecting the two is filled with water. Thus, vibrations resulting from a transfer of the sample dispenser head 200a or from the operation of other mechanisms apply an inertial force to the water inside the passageway, causing a pressure fluctuation. Also, because the water, air bubbles in it, and the passageway structure are elastic, they change in volume due to a pressure fluctuation. However, since the present embodiment is designed to perform a discharge operation after pressure fluctuations have been suppressed, dispensing accuracy is not be affected by vibrations. This makes it possible to perform accurate dispensing and measure the concentration of the substance of interest accurately.

Further, since the present embodiment is designed to perform multiple analyses simultaneously, there is a limit on the amount of time available to wait for vibrations to cease. However, the controller 60 is capable of judging whether an analysis can be completed within a limited amount of time; thus, highly reliable analyses are possible.

DESCRIPTION OF REFERENCE NUMERALS

1: Bellows
2, 3: Permanent magnet
4: Motor
5: Solenoid
6: Diaphragm
7: Pressure sensor
8: Signal processor circuit
9: Nozzle base
10: Nozzle tip
11, 12, 13: Cavity
14: Air vent 15: Casing
16: Bellows drive mechanism
17: Basing means
18: Sample
34: Sample vessel
35: Reaction vessel
36: Reaction disk
37: Sample disk
40: Reagent vessel
41: First reagent disk
42: Second reagent disk
45: Vessel rinse mechanism
50: Light source
51: Spectroscopic optical system
60: Controller
61: Computer
71: Metering pump
72: Tube
73: Drive mechanism
100: Bellows mechanism
200: Dispenser head
201: Suction
202: Transfer of dispenser head
203: Discharge
301: Start of suction
302: End of suction
303: Pressure fluctuation monitoring
304: Presence or absence of pressure fluctuation
305: Start of discharge
306: End of discharge
307: Another discharge needed?
401: Halt
501: Monitoring condition
502: Number of monitorings performed
503: Monitoring time
504: Fluctuation amplitude
505: Alarm
701: Halt

The invention claimed is:

1. An automatic analyzer comprising:
a reaction vessel adapted to receive a sample from a sample vessel and a reagent from a reagent vessel;
a reaction vessel retention mechanism for holding the reaction vessel;
means to subject the sample and the reagent in the reaction vessel to analysis;
a sample dispensing mechanism to draw a sample from the sample vessel into a cavity in the sample dispensing mechanism and to discharge the sample into the reaction vessel;
a nozzle in the sample dispensing mechanism for dispensing the sample, the nozzle having a nozzle cavity;
a pressure altering mechanism in the sample dispensing mechanism for changing the pressure inside the nozzle cavity to discharge the sample into the reaction vessel;
a nozzle transfer mechanism for transferring the nozzle between the sample vessel and the reaction vessel;
a pressure detecting mechanism in the sample dispensing mechanism for detecting the pressure inside the nozzle cavity; and
a control mechanism;
wherein the control mechanism includes:
a liquid-sway detecting function for detecting a liquid sway of the liquid inside the nozzle cavity based on the output from the pressure detecting mechanism; and
a control function for controlling the operation of the pressure altering mechanism based on the output from the liquid-sway detecting function.

2. The automatic analyzer of claim 1, wherein the control mechanism operates such that the liquid drawn by the sample dispensing mechanism is discharged when the liquid sway detecting by the liquid-sway detecting function has become one of equal to and less than a given value.

3. The automatic analyzer of claim 1, further comprising display means for displaying, when the liquid-sway detecting function has not become one of equal to and less than a given value within a given amount of time, a message to that effect.

4. The automatic analyzer of claim 1, further comprising a pressure applying mechanism for applying a pressure to the nozzle cavity based on the liquid-sway detecting function so as to cancel out liquid sway.

5. A sample treatment apparatus comprising:
a sample dispensing mechanism to draw a sample into a cavity in the sample dispensing mechanism;
a nozzle in the sample dispensing mechanism and having a nozzle cavity for dispensing a liquid sample from the nozzle cavity;
a pressure altering mechanism for changing the pressure inside the nozzle cavity;
a nozzle transfer mechanism for transferring the nozzle;
a pressure detecting mechanism for detecting the pressure inside the nozzle cavity; and
a control mechanism;
wherein the control mechanism includes:
a liquid-way detecting function for detecting the liquid sway of the liquid inside of the nozzle cavity based on the output from the pressure detecting mechanism; and
a control function for controlling operation of the nozzle transfer mechanism based on the output from the liquid-sway detecting function.

6. The sample treatment apparatus of claim 5, wherein the control mechanism operates such that the sample drawn into the nozzle cavity by the pressure altering mechanism is discharged when the liquid-sway detected by the liquid sway detecting function has become one of equal to and less than a given value.

7. The sample treatment apparatus of claim 5, further comprising display means for displaying, when the output from the liquid-sway detecting function has not become one of equal to and less than a given value within a given amount of time, a message to that effect.

8. The sample treatment apparatus of claim 5, further comprising a pressure applying mechanism for applying a pressure to the inside of the nozzle based on the output from the liquid-sway detecting mechanism to cancel out liquid sway.

* * * * *